United States Patent
Johnson et al.

(10) Patent No.: US 10,349,891 B2
(45) Date of Patent: Jul. 16, 2019

(54) ANIMATE OBJECT DETECTION SYSTEM AND METHOD OF DETECTING AN ANIMATE OBJECT

(71) Applicant: GM GLOBAL TECHNOLOGY OPERATIONS LLC, Detroit, MI (US)

(72) Inventors: Nancy L. Johnson, Northville, MI (US); Dorel M. Sala, Troy, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 270 days.

(21) Appl. No.: 15/245,890

(22) Filed: Aug. 24, 2016

(65) Prior Publication Data

US 2017/0082507 A1 Mar. 23, 2017

Related U.S. Application Data

(60) Provisional application No. 62/221,355, filed on Sep. 21, 2015.

(51) Int. Cl.
*A61B 5/00* (2006.01)
*A61B 5/11* (2006.01)
*A61B 5/113* (2006.01)

(52) U.S. Cl.
CPC .......... *A61B 5/6892* (2013.01); *A61B 5/1102* (2013.01); *A61B 5/1115* (2013.01); *A61B 5/1135* (2013.01); *A61B 5/6894* (2013.01); *A61B 5/6843* (2013.01); *A61B 2562/0247* (2013.01)

(58) Field of Classification Search
CPC ....... A61B 5/02; A61B 5/0205; A61B 5/6894; A61B 5/1115; A61B 5/1102; A61B 5/1135; A61B 2562/0247; A61B 5/6843
See application file for complete search history.

(56) References Cited

U.S. PATENT DOCUMENTS

| | | | |
|---|---|---|---|
| 2009/0005936 A1* | 1/2009 | Browne | B60R 25/1004 701/45 |
| 2010/0101022 A1* | 4/2010 | Riley | A61G 7/0514 5/600 |
| 2014/0278229 A1* | 9/2014 | Hong | A63B 71/06 702/160 |
| 2015/0164391 A1* | 6/2015 | Hernandez-Rosas | A61B 5/14532 600/365 |
| 2015/0313475 A1* | 11/2015 | Benson | A61B 5/6893 297/217.3 |

\* cited by examiner

*Primary Examiner* — Justin Seo
*Assistant Examiner* — John M Royston
(74) *Attorney, Agent, or Firm* — Quinn IP Law

(57) ABSTRACT

An animate object detection system includes an apparatus configured for supporting an animate object and a sensor disposed in physical communication with the apparatus. The sensor includes a piezoelectric material and is configured for producing an electric signal in response to a force applied to the apparatus by the animate object. The system also includes a signal conditioner disposed in electrical communication with the sensor and configured for manipulating the electric signal and producing an output signal, and a receiver configured for receiving the output signal and generating an indicator signal. A method of detecting an animate object is also disclosed.

10 Claims, 4 Drawing Sheets

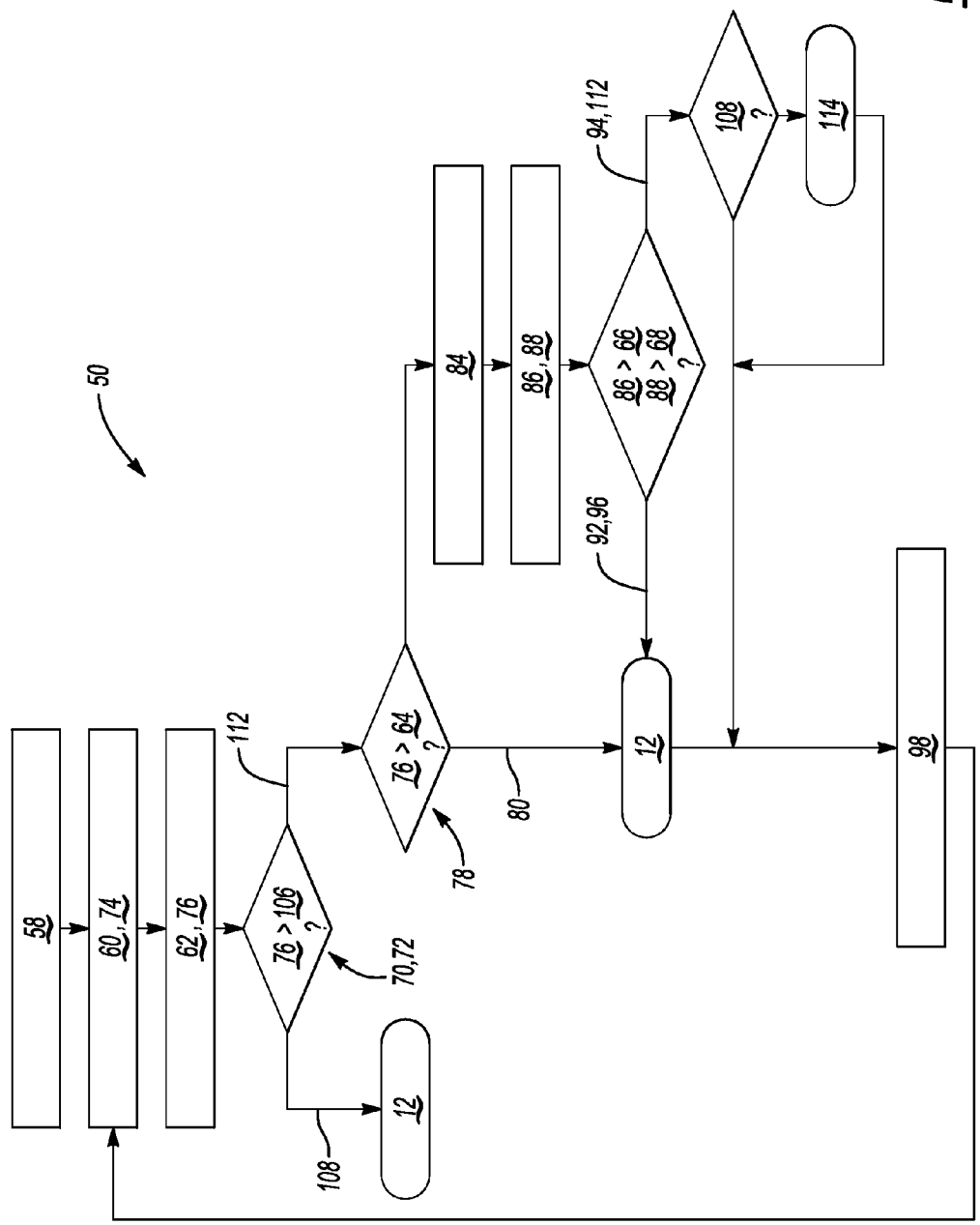

ANIMATE OBJECT DETECTION SYSTEM AND METHOD OF DETECTING AN ANIMATE OBJECT

CROSS-REFERENCE TO RELATED APPLICATIONS

This application claims the benefit of U.S. Provisional Application No. 62/221,355, filed on Sep. 21, 2015, which is hereby incorporated by reference in its entirety.

TECHNICAL FIELD

The disclosure relates to an animate object detection system and to a method of detecting an animate object.

BACKGROUND

Various transport apparatus, including passenger, performance, industrial, and mobility vehicles as well as boats, planes, buses, ambulances, hospital beds, wheelchairs, and the like are used for conveying occupants. For example, vehicle bodies typically define an enclosed passenger compartment and may include one or more seats configured to support occupants. The passenger compartment may be accessible through doors and windows that are lockable to prevent unauthorized entry into the passenger compartment when the vehicle is left unattended.

Similarly, other transport apparatus such as wheelchairs, strollers, gurneys, and the like are generally configured to transport an occupant for whom walking is difficult. Such transport apparatus generally include a seat or occupant support surface and may be pushed by an attendant during occupant transport. During some uses, the transport apparatus may be both occupied and unattended. For example, an occupant may rest on a gurney while the gurney is unattended.

SUMMARY

An animate object detection system includes an apparatus configured for supporting an animate object, and a sensor disposed in physical communication with the apparatus. The sensor includes a piezoelectric material and is configured for producing an electric signal in response to a force applied to the apparatus by the animate object. The animate object detection system also includes a signal conditioner disposed in electrical communication with the sensor and configured for manipulating the electric signal and producing an output signal. In addition, the animate object detection system includes a receiver configured for receiving the output signal and generating an indicator signal.

In one embodiment, the animate object detection system includes a seat system configured for restraining the animate object, and an apparatus configured for supporting the seat system. Further, the animate object detection system includes a sensor disposed within the seat system and including a piezoelectric material. The sensor is configured for producing an electric signal in response to a force applied to the seat system by the animate object. The animate object detection system also includes a signal conditioner disposed in electrical communication with the sensor and configured for receiving the electric signal and producing an output signal. In addition, the animate object detection system includes a transmitter configured for wirelessly transmitting the output signal, and a receiver configured for wirelessly receiving the output signal and generating an indicator signal.

A method of detecting an animate object includes determining a threshold power level, a threshold breathing rate, and a threshold heart rate. The method also includes measuring a signal power level of an electric signal produced by a sensor in response to a force applied to an apparatus upon which the animate object is disposed. The sensor is disposed in physical communication with the apparatus and includes a piezoelectric material. The method also includes detecting one of a first condition in which the signal power level is greater than or equal to the threshold power level to thereby detect the animate object, and a second condition in which the signal power level is less than the threshold power level. After detecting the second condition, the method includes conditioning the electric signal to thereby calculate a breathing rate and a heart rate. After conditioning, the method includes detecting at least one of a third condition in which the breathing rate is greater than or equal to the threshold breathing rate to thereby detect the animate object, a fourth condition in which the breathing rate is less than the threshold breathing rate, a fifth condition in which the heart rate is greater than or equal to the threshold heart rate to thereby detect the animate object, and a sixth condition in which the heart rate is less than the threshold heart rate. After detecting at least one of the first condition, the third condition, and the fifth condition, the method includes generating an indicator signal.

The above features and advantages and other features and advantages of the present disclosure will be readily apparent from the following detailed description of the preferred embodiments and best modes for carrying out the present disclosure when taken in connection with the accompanying drawings and appended claims.

BRIEF DESCRIPTION OF THE DRAWINGS

FIG. 7 is a flowchart diagram of another embodiment of the method of FIG. 6.

DETAILED DESCRIPTION

Figure 1:
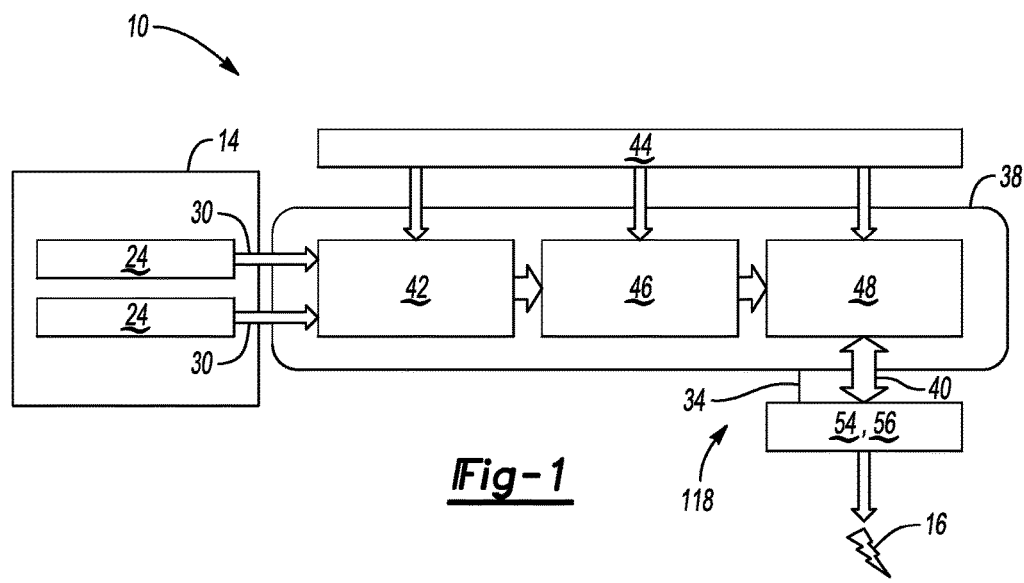
FIG. 1 is a schematic illustration of an animate object detection system.
Figure 2:
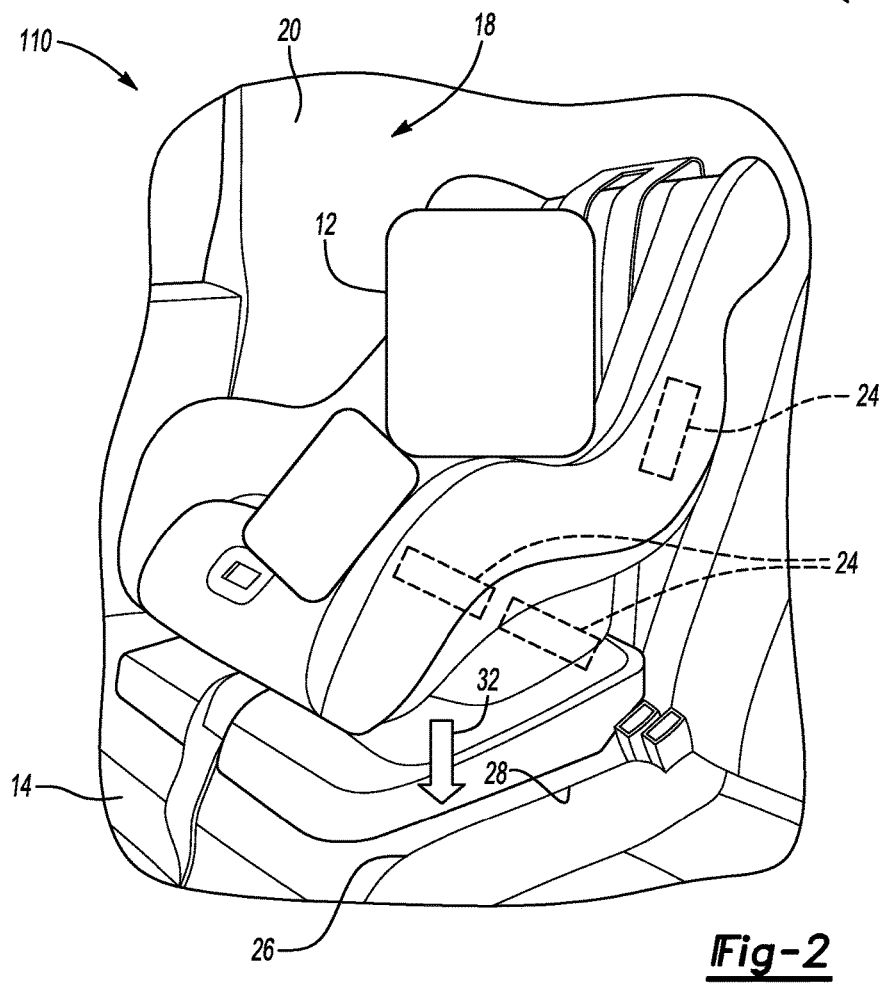
FIG. 2 is a schematic illustration of another embodiment of the animate object detection system of FIG. 1.

Referring to the Figures, wherein like reference numerals refer to like elements, an animate object detection system 10, 110 is shown generally in FIGS. 1-5. Referring to FIG. 2, the animate object detection system 110 may be useful for detecting a presence of an animate object 12 disposed on an apparatus 14. The animate object 12 may be, for example, a child, an animal, a patient of a medical or care facility, or an inmate of a correctional facility. Further, the apparatus 14 may be a vehicle, such as an automotive passenger vehicle, a wheelchair, a stroller, a wagon, a bed, a gurney, or a surface. As set forth in more detail below, the animate object detection system 10, 110 provides an indicator signal 16 (FIG. 1) or alert to indicate the presence of the animate object 12. As such, the animate object detection system 10, 110 may communicate or interface with other systems, such as, but not limited to, restraint reminder systems, air bag systems, first responder communication networks, central monitoring stations, and the like.

Referring now to FIG. 1, the animate object detection system 10, 110 includes the apparatus 14 configured for supporting the animate object 12 (FIG. 2). As a non-limiting example, the apparatus 14 may be a portion of an automotive vehicle 20 (FIG. 2). For example, the apparatus 14 may be a rear seat disposed within the passenger compartment 18 (FIG. 2) of the vehicle 20. In another example, the apparatus 14 may be a rear portion of a van or sport utility vehicle where the animate object 12, e.g., a pet, may sit and/or be restrained. Alternatively, the apparatus 14 may be a seat portion of another vehicle type, such as, but not limited to, an industrial vehicle, a bus, an aircraft, and the like. As another non-limiting example, the apparatus 14 may be a seating surface of a wheelchair or stroller, or may be a sleeping surface of a bed or cot.

Figure 3:
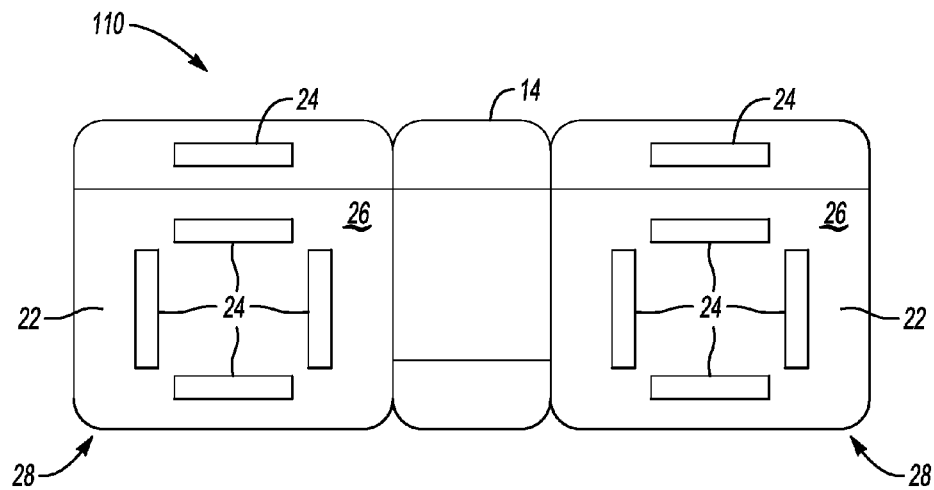
FIG. 3 is a schematic illustration of a top view of the animate object detection system of FIG. 2.
Figure 4:
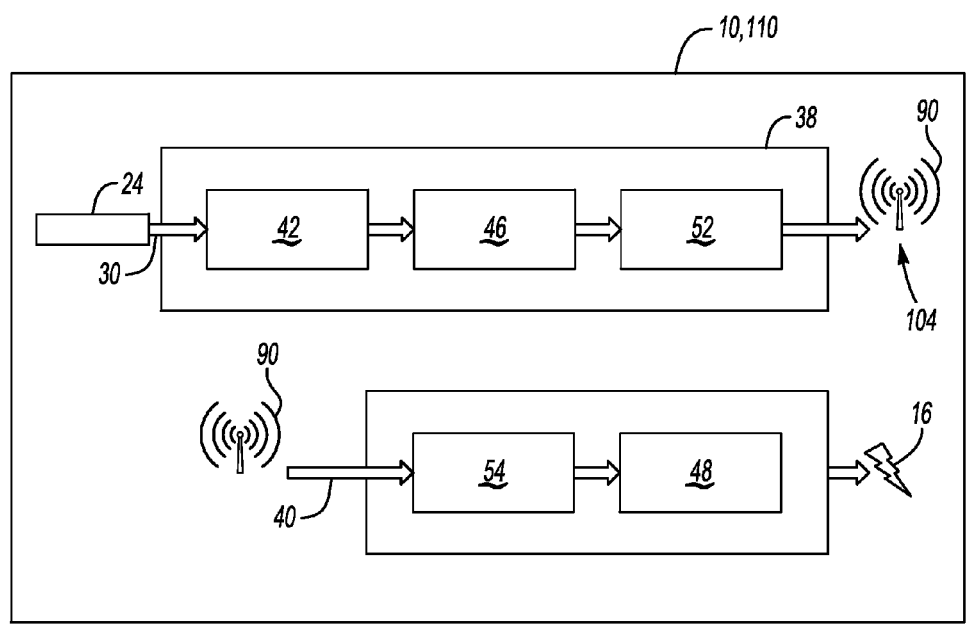
FIG. 4 is a schematic illustration of an additional embodiment of the animate object detection system of FIGS. 1 and 2.

In one embodiment described with reference to FIG. 3, the animate object detection system 110 includes a seat system 22 configured for restraining the animate object 12 (FIG. 2). For example, the seat system 22 may be characterized as a child restraint seat system or car seat system. For this embodiment, the apparatus 14 may be the rear seat of the vehicle 20 or a retaining structure (not shown) of a stroller, and the seat system 22 may be disposed on or in contact with the apparatus 14. It should be noted that for this embodiment, the seat system 22 may be selectively removable from the apparatus 14 and may be a portable and/or removable child seating system, a storage bag for a hospital bed or stroller, and the like. In addition, the seat system 22 may be a pet bed or container. Referring again to FIG. 1, the animate object detection system 10, 110 also includes a sensor 24 disposed in physical communication with the apparatus 14. The sensor 24 may be disposed adjacent to the apparatus 14, e.g., in immediate proximity to the apparatus 14, such that the sensor 24 may detect a force 32 (FIG. 2) or pressure applied by the animate object 12 to the apparatus 14. For example, the sensor 24 may be disposed on a surface 26, 28 (FIG. 2) of the apparatus 14. More specifically, the apparatus 14 may have a first surface 26 disposed adjacent the animate object 12 and a second surface 28 disposed opposed the first surface 26. The sensor 24 may be disposed adjacent the second surface 28. That is, as a non-limiting example, the sensor 24 may be disposed on or contact the second surface 28 or may be disposed within the apparatus 14 underneath the second surface 28.

Referring again to FIG. 2, for embodiments including the seat system 22 (FIG. 3) configured for restraining the animate object 12, the sensor 24 may be disposed within the seat system 22. That is, the sensor 24 may be disposed underneath one or more padding and fabric layers of the seat system 22, and during use, the animate object 12 may sit upon the padding and/or fabric layers that directly cover the sensor 24. Therefore, in this embodiment, the sensor 24 may be configured for producing an electric signal 30 (FIG. 1) in response to the force 32 applied to the seat system 22 by the animate object 12. That is, the sensor 24 is configured for producing the electric signal 30 in response to the force 32 applied to the apparatus 14 by the animate object 12.

The sensor 24 includes a piezoelectric material. As used herein, the terminology piezoelectric material refers to a material which generates an electrical charge or current when deformed or displaced as a result of mechanical stress. Conversely, the material may change shape and apply a force or pressure when subjected to an electrical charge. Suitable non-limiting examples of piezoelectric materials include piezoceramics configured as fibers, unimorphs, bimorphs, patches, etc.; electroactive polymers (EAP) configured as thin and flexible patches; magnetorestrictive composites in which flexure of the magnetorestrictive composite generates a changing magnetic field and induces a current in a coil; magnetostrictive fibers in which vibration of the magnetorestrictive fibers generates a changing magnetic field; ionic polymer metal composites; magnetic shape memory alloys (MSMA); multiferroic materials such as hybrid piezo/magnetorestrictive materials; ferroelectret foams; resonant magnet/coil combinations; and combinations thereof. In one embodiment, the piezoelectric material is a polyvinylidene fluoride polymer. Further, it is to be appreciated that the animate object detection system 10, 110 may include a plurality of sensors 24, e.g., one or more sensors 24 as shown generally in FIG. 3, disposed adjacent the second surface 28 and each including a piezoelectric material.

In addition, the animate object detection system 10, 110 may be scalable and may include any number of surfaces 26, 28 and/or seat systems 22. For example, the animate object detection system 110 may include a plurality of seat systems 22 and one or more of the plurality of seat systems 22 may be removable from the apparatus 14.

Referring again to FIG. 1, the sensor 24 may be configured to detect a condition. In the embodiments depicted, the condition detected by the sensor 24 may be movement of the animate object 12 (FIG. 2) inside the passenger compartment 18 (FIG. 2) of the vehicle 20 (FIG. 2). However, it is noted that a sensitivity or capability of the sensor 24 may be selected such that the sensor 24 may detect very slight movement of the animate object 12 while the apparatus 14 is at rest and/or unattended. For example, the sensor 24 may sense movement, forces 32 (FIG. 2), and/or pressure changes resulting from movement of a chest of the animate object 12 and associated with a breathing rate 86 (FIG. 6) or heart rate 88 (FIG. 6) of the animate object 12, as set forth in more detail below.

As described with continued reference to FIG. 1, the animate object detection system 10, 110 also includes a signal conditioner 38. The signal conditioner 38 is disposed in electrical communication with the sensor 24 and is configured for manipulating the electric signal 30 and producing an output signal 40. That is, the signal conditioner 38 may manipulate the electric signal 30 to prepare the electric signal 30 for subsequent processing. More specifically, the signal conditioner 38 may be an assembly configured for conditioning the electric signal 30 to thereby convert the electric signal 30 into the output signal 40. For example, the signal conditioner 38 may condition or prepare a difficult-to-read electric signal 30 into an easily-readable output signal 40.

The signal conditioner 38 may include an amplifier 42. The amplifier 42 may increase an overall magnitude of the electric signal 30. For example, the animate object detection system 10, 110 may include a power supply 44 and the amplifier 42 may modulate an output, e.g., a voltage, of the power supply 44. The amplifier 42 may be a separate stand-alone component, i.e., a separate piece of equipment, within the signal conditioner 38 or may be an electrical circuit integrated within the signal conditioner 38.

Alternatively or additionally, the signal conditioner 38 may include an analog-to-digital converter 46. The analogto-digital converter 46 may convert the voltage from the amplifier 42 to a digital signal that represents the amplitude of the voltage. The analog-to-digital converter 46 may periodically sample an input, e.g., the voltage from the amplifier 42, to produce a sequence of discrete-time and discrete-amplitude digital values.

The signal conditioner 38 may also include a processor 48 configured for manipulating the electric signal 30. The processor 48 may be characterized as one or more digital computer devices disposed in electrical communication with one or more components of the animate object detection system 10, 110, and may be configured to withstand a comparatively harsh operating environment which may include moisture, contaminants, and/or high temperature.

Structurally, the processor 48 may be disposed in operative communication with tangible, non-transitory memory (not shown), e.g., read-only memory (ROM), flash memory, optical memory, additional magnetic memory, etc. The processor 48 may also include any required random access memory (RAM), electrically-programmable read-only memory (EPROM), a high-speed clock, analog-to-digital (A/D) and/or digital-to-analog (D/A) circuitry, and any input/output circuitry or devices, as well as any appropriate signal conditioning and buffer circuitry. Instructions for executing a method 50 (FIGS. 6 and 7) of detecting the animate object 12 may be recorded in the memory and executed as needed via the processor 48. That is, one or more individual control algorithms of the processor 48, such as instructions embodying the method 50, may be stored in memory and automatically executed via the processor 48 to provide control functionality.

Therefore, the processor 48 may include all software, hardware, memory, algorithms, connections, and the like necessary to monitor the apparatus 14 to detect the animate object 12. The one or more sensors 24 may be physically coupled to the apparatus 14, and the one or more sensors 24 may be disposed in operable communication with the processor 48. Therefore, the method 50 may be embodied as software or firmware associated with the processor 48 and/or the signal conditioner 38. It is to be appreciated that the processor 48 may also include any device capable of analyzing data from various inputs, e.g., the one or more sensors 24, comparing data, completing necessary decisions, etc. As set forth in more detail below, a possible control action resulting from execution of the method 50 is an indication of the animate object 12 disposed on the apparatus 14 for an automotive or non-automotive application.

Figure 5:
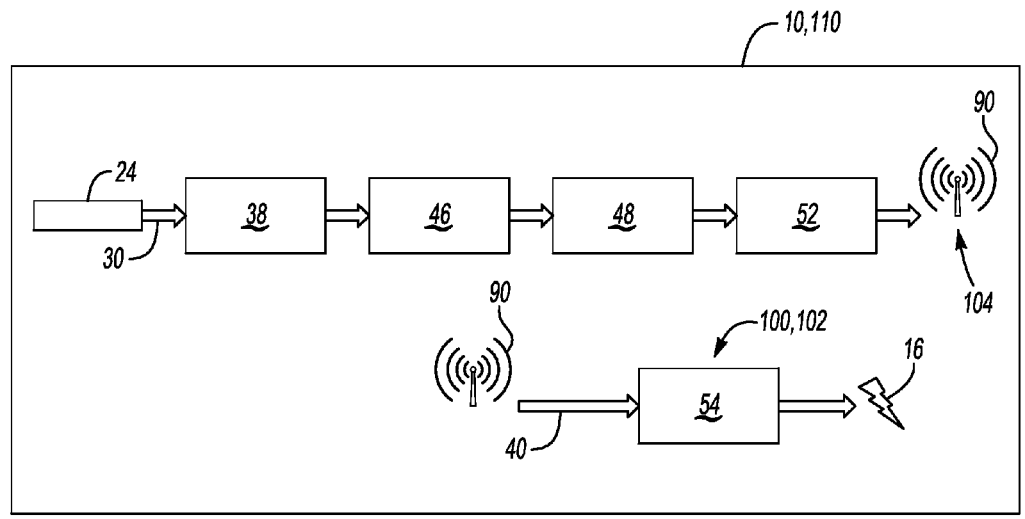
FIG. 5 is a schematic illustration of a further embodiment of the animate object detection system of FIGS. 1, 2, and 4.

Referring now to FIG. 5, for embodiments in which the animate object detection system 110 includes the sensor 24 disposed within the seat system 22 (FIG. 3), the animate object detection system 110 also includes a transmitter 52 configured for wirelessly transmitting the output signal 40. The transmitter 52 may include a data encoder and may be configured to selectively transmit a wireless signal 90 in response to the electric signal 30 generated by the sensor 24, i.e., when the sensor 24 is deformed or displaced and thereby detects the presence of the animate object 12. The wireless signal 90 in one embodiment may be an electromagnetic wave in the radiofrequency spectrum.

Referring again to FIG. 1, the animate object detection system 10, 110 also includes a receiver 54 configured for receiving the output signal 40 and generating an indicator signal 16. The receiver 54 may be any suitable device capable of receiving the output signal 40 as an input and generating the indicator signal 16 as an output. For example, the receiver 54 may be configured for wirelessly receiving the output signal 40. Alternatively, the receiver 54 may be operatively connected to the signal conditioner 38 by a wire 34. That is, the animate object detection system 10, 110 may be characterized as a wireless system, a wired system, or a hybrid system in which the output signal 40 is, under certain conditions or configurations, transmitted via the wire 34 and, under other conditions or configurations, is transmitted wirelessly. As non-limiting examples, the receiver 54 may be a control system 56, a cellular communications device (not shown), a key fob, or a patient monitoring system.

In some embodiments, the receiver 54 may be a wireless receiver that is positioned with respect to the transmitter 52 to receive the output signal 40. For example, as described with reference to FIG. 4, the receiver 54 may include the processor 48 configured for manipulating the output signal 40. The receiver 104 may be operatively connected to a processor 48, such as via conductive wires, to communicate to the processor 48 whether the output signal 40 is being transmitted by the transmitter 52. Thus, the sensor 24 may be operatively connected to the processor 48 for communication via transmitter 52 and receiver 54.

Referring again to FIGS. 1, 4, and 5, the indicator signal 16 may be a visual signal, an auditory signal, and/or an electronic signal. That is, the indicator signal 16 may be useful for alerting an attendant to condition, particularly to the presence of the animate object 12 disposed on the apparatus 14. For example, the indicator signal 16 may be an image, shape, and/or color displayed on a cellular communications device. Additionally or alternatively, the indicator signal 16 may be auditory, such as a bell or chime or honk. Further, the indicator signal 16 may be an electronic signal conveyed to memory or a computing device upon detection of the animate object 12, which may in turn direct an electronic signal to police or monitoring personnel.

Referring again to FIG. 1, the animate object detection system 10, 110 may also include a control system 56. The control system 56 may be programmed to inquire whether the sensor 24 is deformed or displaced as a result of the force 32 (FIG. 2) from the animate object 12 disposed on the apparatus 14. The control system 56 may determine the answer to the inquiry by determining whether the signal conditioner 38 is transmitting the output signal 40. If the output signal 40 is present, then the control system 56 may inquire whether at least one other predetermined condition exists. Exemplary predetermined conditions for automotive applications may include whether an engine is off, whether an ignition switch is in the off position, whether any of the vehicle doors is open, whether a transmission selector is in its "park" position, whether any of the vehicle doors has been opened within a predetermined period of time prior to the inquiry, whether a cellular communications device is in a vicinity of the animate object detection system 10, 110, whether the animate object detection system 10, 110 is connected or paired to the cellular communications device, etc. Exemplary predetermined conditions for non-automotive applications may include whether a wheel brake is actuated, whether a room door is opened, etc.

Although not shown, the animate object detection system 10, 110 may also include other sensors configured to detect the at least one other predetermined condition. For example, although not shown, the animate object detection system 10, 110 may include a temperature sensor that is configured to monitor a temperature surrounding the apparatus 14, e.g., inside the passenger compartment 18 (FIG. 2). The temperature sensor may be operatively connected to the control system 56, such as via an electrically conductive medium, a wireless radio frequency connection, etc., and may be configured to communicate the temperature surrounding the apparatus 14 to the control system 56.

It is noted that communication by the temperature sensor may include both the presence and the absence of the electric signal 30 when the absence of the electric signal 30 is indicative of a state of a component. For example, the temperature sensor may be configured to transmit a signal to the control system 56 only when the temperature of the passenger compartment 18 is above a first predetermined temperature or below a second predetermined temperature, and not when the temperature of the passenger compartment 18 is between the first and second predetermined temperatures.

Other sensors or detectors may monitor the status of other apparatus components and conditions, and may communicate the status of the other apparatus components and conditions to the control system 56. For example, other sensors may communicate to the control system 56 whether the engine (not shown) is running, whether the ignition switch is in the on or off position, whether a door is open or closed, whether the transmission selector is in its park position, whether the apparatus 14 is stationary, whether an apparatus brake is set, whether a room door is open, whether a cellular communications device is in a vicinity of the animate object detection system 10, 110, whether the animate object detection system 10, 110 is connected or paired to the cellular communications device, etc.

The control system 56 may be operatively connected to one or more apparatus components, such as via conductive wires, to selectively transmit command signals to the apparatus components. The apparatus components may be responsive to the command signals from the control system 56 to cause a physical change to the apparatus 14, such as movement of an apparatus component, activation of the apparatus component, etc. The control system 56 may also be operatively connected to the transmitter 52 to selectively cause the transmitter 52 to transmit the wireless signal 90 to an offboard station (not shown). The wireless signal 90 may be transmitted directly from the transmitter 52 to the offboard station, or may be transmitted indirectly, such as by a satellite relay (not shown), cellular telephone system (not shown), etc. The receiver 54 may also be configured to receive signals from the offboard station and may be operatively connected to the control system 56.

For example, for automotive applications, the control system 56 may transmit the command signal to a window regulator of the vehicle 20 to cause the regulator to move a door window from a closed position to an open position, particularly if the temperature of the passenger compartment 18 is above a predetermined temperature. The control system 56 may transmit the command signal to the doors of the vehicle 20 to unlock the doors. The control system 56 may transmit the command signal to an alert system that produces an audible sound in response to the command signal. In one example, the audio system speakers of the vehicle 20 may generate the audible sound (particularly in conjunction with opening the windows). The control system 56 may transmit the command signal to child locks of the vehicle 20 to disengage the child locks. The control system 56 may transmit command signals to actuators of the vehicle 20 to open doors, a sunroof (not shown), the rear decklid, a rear liftgate (not shown), etc. The control system 56 may transmit the command signal to flash the headlights or tail lights of the vehicle 20.

For non-automotive or automotive applications, the control system 56 may transmit the command signal to an offsite station or personnel. For example, the control system 56 may communicate with the offsite station, such as by transmitting the command signal to the transmitter 52, to cause the transmitter 52 to transmit the command signal to the offboard station to thereby alert the offboard station that the animate object 12 is disposed on the apparatus 14. The command signal may also include information such as the location of the apparatus 14, a unique identifier of the apparatus 14, or a registered owner of the apparatus 14. The offboard station may then transmit command signals to the receiver 54 so that the receiver 54 transmits instruction signals to the control system 56. The control system 56 may in turn be responsive to the instruction signals and transmit other command signals.

The offboard station may be automated, or may be operated by a human operator. The offboard station may determine which apparatus components are commanded by the command signals based on varying circumstances, and may also perform other steps in response to receiving the command signal, such as determining the location of the apparatus 14 and notifying an entity of the condition of the apparatus 14. The entity may be, for example, police or another law enforcement agency, the registered owner of the apparatus 14 (via the registered owner's cellular telephone, key fob, handheld display, or other wireless communication device), a business located in close proximity to the apparatus 14 (via telephone), persons outside the apparatus 14 (e.g., notified by opening vehicle windows and causing a message to be broadcast via the vehicle's audio system speakers), etc. Accordingly, it may be desirable for the animate object detection system 10, 110 to include a global positioning system (GPS) such that the location of the apparatus 14 may be transmitted to the offsite station. Alternatively, cellular telephone towers may be used to triangulate position.

For automotive applications, the control system 56 may also inquire, prior to transmitting command signals, whether a first predetermined amount of time has passed since the occurrence of some event, such as the closure of a vehicle door or the movement of the ignition switch from the on position to the off position. If the control system 56 determines that the first predetermined amount of time has passed, then the control system 56 may transmit the command signal. The control system 56 may also inquire whether a second predetermined amount of time greater than the first predetermined time has passed since the occurrence of the event. If the control system 56 determines that the second predetermined amount of time has passed, then the control system 56 may transmit the command signal.

Figure 6:
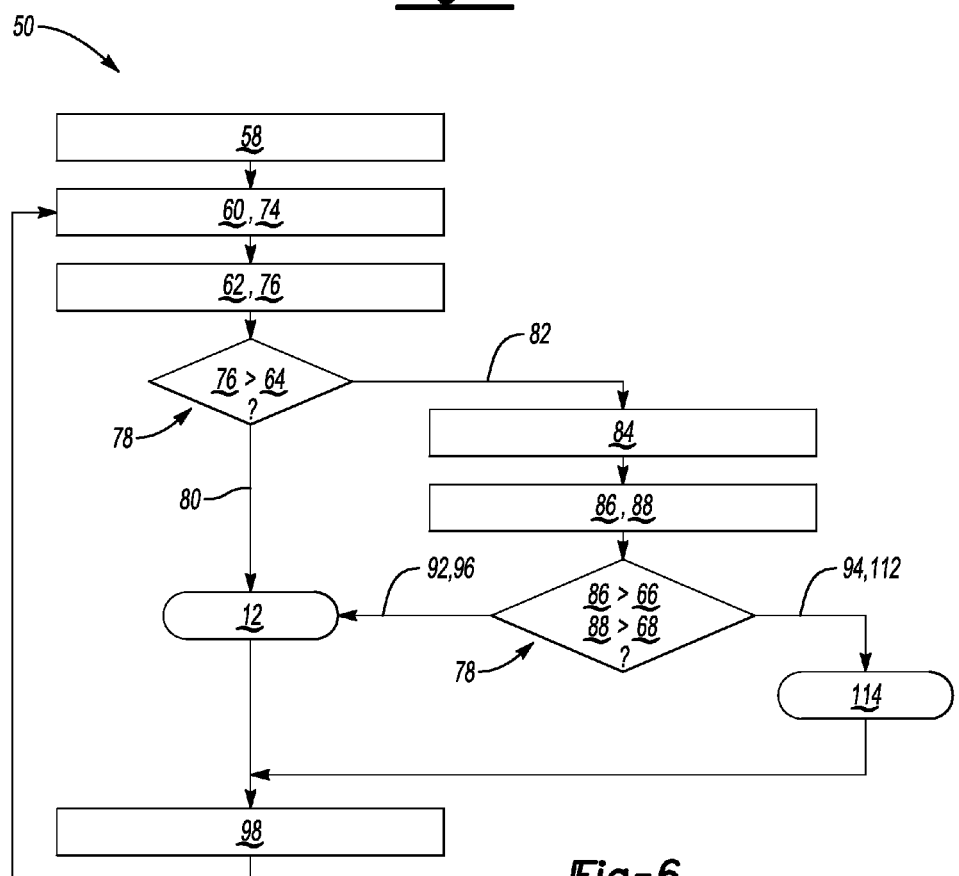
FIG. 6 is a flowchart diagram of a method of detecting an animate object.

Referring now to FIGS. 6 and 7, a method 50 of detecting the animate object 12 is illustrated schematically in flowchart format. As described with reference to FIG. 6, the method 50 of detecting the animate object 12 may include initializing 58 the animate object detection system 10, 110 (FIG. 1) by selecting a sampling frequency and sampling duration. The method 50 may also include acquiring 60 data from the sensor 24 (FIG. 1) to ensure that the sensor 24 is functioning properly.

In addition, the method 50 may also include, prior to determining 62, ascertaining 72 (FIG. 7) an outset condition 70 (FIG. 7) in which the apparatus 14 (FIG. 2) is stationary. That is, the method 50 may include ascertaining 72 whether, for example, the vehicle 20 is parked or a gurney is stationary.

Further, referring again to FIG. 6, the method 50 includes determining 62 a threshold power level 64, a threshold breathing rate 66, and a threshold heart rate 68. The threshold power level 64 may be selected according to a minimal power level required to power the sensor 24 (FIG. 1). The threshold breathing rate 66 may correspond to normal, at-rest breathing of the animate object 12 and may have a frequency of from about 0.25 Hz to about 0.33 Hz. The threshold heart rate 68 may correspond to a normal resting pulse of the animate object 12 and may have a frequency of from about 1.0 Hz to about 1.67 Hz.

The method 50 also includes measuring 74 a signal power level 76 of the electric signal 30 produced by the sensor 24 in response to the force 32 applied to the apparatus 14 upon which the animate object 12 is disposed. Further, the method 50 includes detecting 78 one of a first condition 80 in which the signal power level 76 is greater than or equal to the threshold power level 64 to thereby detect the animate object 12, and a second condition 82 in which the signal power level 76 is less than the threshold power level 64. If the first condition 80 is detected, the animate object detection system 10, 110 may generate the indicator signal 16 to alert an attendant that the animate object 12 is disposed on the apparatus 14. However, it is to be appreciated that for patient monitoring applications, the indicator signal 16 may include silence to indicate that the animate object 12 is disposed on the apparatus 14. That is, for some applications, the indicator signal 16 may only be audible when the animate object 12 is not disposed on the apparatus 14.

After detecting 78 the second condition 82, the method 50 also includes conditioning 84 the electric signal 30 to thereby calculate a breathing rate 86 and a heart rate 88. For example, conditioning 84 may include applying a fast Fourier transform (FFT) algorithm to the electric signal 30 to extract the breathing rate 86 and the heart rate 88. The extracted breathing rate 86 and heart rate 88 may then be compared to threshold values 66, 68.

That is, after conditioning 84, the method 50 includes detecting 78 at least one of: a third condition 92 in which the breathing rate 86 is greater than or equal to the threshold breathing rate 66 to thereby detect the animate object 12; a fourth condition 94 in which the breathing rate 86 is less than the threshold breathing rate 66; a fifth condition 96 in which the heart rate 88 is greater than or equal to the threshold heart rate 68 to thereby detect the animate object 12; and a sixth condition 112 in which the heart rate 88 is less than the threshold heart rate 68. If the third condition 92 or fifth condition 96 is detected, the animate object detection system 10, 110 may generate the indicator signal 16 to alert an attendant that the animate object 12 is disposed on the apparatus 14. However, for patient monitoring applications, the indicator signal 16 may include silence to indicate that the animate object 12 is disposed on the apparatus 14.

As described with reference to FIG. 5, for embodiments including the receiver 54 configured for wirelessly receiving the output signal 40, the method 50 may additionally include, prior to detecting 78, positioning 100 the receiver 54 configured for wireless communication within a predetermined distance of the apparatus 14. For example, the receiver 54 may be a cellular telephone positioned within the predetermined distance of the apparatus 14.

After detecting 78 at least one of the first condition 80, the third condition 92, and the fifth condition 96, the method 50 includes generating 98 the indicator signal 16. For embodiments including the receiver 54 configured for wirelessly receiving the output signal 40 as described with reference to FIG. 6, the method 50 may also include, after positioning 100 (FIG. 5) and concurrent to generating 98, verifying 102 (FIG. 5) that the receiver 54 is disposed within the predetermined distance, i.e., within range of the transmitter 52. That is, the method 50 may further include, after generating 98, wirelessly transmitting 104 (FIGS. 4 and 5) the wireless signal 90 to the receiver 54. Alternatively, the method 50 may further include, after generating 98, transmitting 118 (FIG. 1) the indicator signal 16 to the receiver 54 via the wire 34.

Referring now to FIG. 7, in another embodiment, the method 50 may include determining 62 an outset power level 106, which may correspond to whether an animate object 12 is latched into the seat system 22. Further, the method 50 may include ascertaining 72 one of: a secured condition 108 in which the signal power level 76 is greater than or equal to the outset power level 106 to thereby detect the animate object 12, and an unsecured condition 114 in which the signal power level 76 is less than the outset power level 106. The secured condition 108 may correspond to a condition in which the animate object 12 is secured onto or into the apparatus 14, and the unsecured condition 114 may correspond to a condition in which the animate object is not latched or restrained onto or into the apparatus 14. Detecting one of the first condition 80 and the second condition 82 may be subsequent to ascertaining 72 the unsecured condition 114. That is, the method 50 may include detecting 78 one of the first condition 80 and the second condition 82 after ascertaining 72 the unsecured condition 114.

For this embodiment, the method 50 includes, after detecting 78 at least one of the secured condition 108, the first condition 80, the third condition 92, and the fifth condition 96, generating 98 the indicator signal 16. Further, the method 50 may include, after detecting 78 at least one of the fourth condition 94 and the sixth condition 112, ascertaining 72 one of the secured condition 108 and the unsecured condition 114. That is, ascertaining 72 one of the secured condition 108 and the unsecured condition 114 may be subsequent to detecting 78 at least one of the fourth condition 94 and the sixth condition 112. As such, the method 50 may continuously monitor whether the animate object 12 is detected.

Therefore, the animate object detection system 10, 110 provides robust and repeatable monitoring and detection of the animate object 12 on the apparatus 14. As set forth above, during operation, the animate object detection system 10, 110 may compare data from the sensor 24 obtained while the apparatus 14 is moving and stationary, and while the animate object 12 is and is not disposed on the seat system 22. Further, the animate object detection system 10, 110 may detect a beginning of travel of the apparatus 14, an initial seating of the animate object 12 on the apparatus 14 or seat system 22, and an end of travel of the apparatus 14. By conditioning 84 the electric signal 30 generated by the sensor 24, the animate object detection system 10, 110 may alert an attendant to a change in status of the animate object 12.

While the best modes for carrying out the disclosure have been described in detail, those familiar with the art to which this disclosure relates will recognize various alternative designs and embodiments for practicing the disclosure within the scope of the appended claims.

The invention claimed is:

1. A method of detecting an animate object on a seat system of an apparatus, the method comprising:
   ascertaining a beginning of travel condition in which the seat system is non-stationary;
   after ascertaining the beginning of travel condition, ascertaining an outset condition in which the seat system is stationary;
   after ascertaining the outset condition, measuring a signal power level of an electric signal produced by a sensor in response to a force applied to the seat system upon which the animate object is disposed, wherein the sensor is disposed in physical communication with the apparatus and includes a piezoelectric material;

determining:
- a threshold power level corresponding to a minimal power level required to power the sensor;
- a threshold breathing rate corresponding to an at-rest breathing of the animate object; and
- a threshold heart rate corresponding to a resting pulse of the animate object;

detecting either of:
- a first condition in which the signal power level is greater than or equal to the threshold power level to thereby detect the animate object; and
- a second condition in which the signal power level is less than the threshold power level;

subsequent to detecting either of the first condition and the second condition, conditioning the electric signal to thereby calculate a breathing rate and a heart rate;

after conditioning, detecting at least one of:
- a third condition in which the breathing rate is greater than or equal to the threshold breathing rate to thereby detect the animate object on the seat system;
- a fourth condition in which the breathing rate is less than the threshold breathing rate;
- a fifth condition in which the heart rate is greater than or equal to the threshold heart rate to thereby detect the animate object on the seat system; and
- a sixth condition in which the heart rate is less than the threshold heart rate; and after detecting at least one of the first condition, the third condition, and the fifth condition, generating an indicator signal to indicate a presence of the animate object on the seat system.

2. The method of claim 1, wherein conditioning includes applying a fast Fourier transform algorithm to the electric signal to extract the breathing rate and the heart rate.

3. The method of claim 1, further including, prior to detecting at least one of the third condition, the fourth condition, the fifth condition, and the sixth condition, positioning a receiver configured for wireless communication within a predetermined distance of the apparatus.

4. The method of claim 3, further including, after positioning and concurrent to generating, verifying that the receiver is disposed within the predetermined distance.

5. The method of claim 1, further including, after generating, wirelessly transmitting the indicator signal to a receiver configured for wireless communication.

6. The method of claim 1, further including, after generating, transmitting the indicator signal to a receiver via a wire.

7. The method of claim 1, further including determining an outset power level.

8. The method of claim 7, further including ascertaining one of:
- a secured condition in which the signal power level is greater than or equal to the outset power level to thereby detect the animate object; and
- an unsecured condition in which the signal power level is less than the outset power level.

9. The method of claim 8, wherein detecting either of the first condition and the second condition is subsequent to ascertaining the unsecured condition.

10. The method of claim 9, wherein ascertaining one of the secured condition and the unsecured condition is subsequent to detecting at least one of the fourth condition and the sixth condition.

* * * * *